US011345937B2

(12) United States Patent
Song et al.

(10) Patent No.: US 11,345,937 B2
(45) Date of Patent: May 31, 2022

(54) **CONSTRUCTION OF *MUCOR CIRCINELLOIDES* CELL FACTORY FOR PRODUCING STEARIDONIC ACID AND FERMENTATION TECHNOLOGY THEREOF**

(71) Applicant: SHANDONG UNIVERSITY OF TECHNOLOGY, Zibo (CN)

(72) Inventors: Yuanda Song, Zibo (CN); Md. Ahsanul Kabir Khan, Zibo (CN); Junhuan Yang, Zibo (CN); Yao Zhang, Zibo (CN); Wu Yang, Zibo (CN); Shaoqi Li, Zibo (CN)

(73) Assignee: SHANDONG UNIVERSITY OF TECHNOLOGY, Shandong (CN)

( * ) Notice: Subject to any disclaimer, the term of this patent is extended or adjusted under 35 U.S.C. 154(b) by 0 days.

(21) Appl. No.: 17/120,160

(22) Filed: Dec. 12, 2020

(65) Prior Publication Data

US 2021/0102225 A1  Apr. 8, 2021

Related U.S. Application Data

(63) Continuation of application No. PCT/CN2019/124014, filed on Dec. 9, 2019.

(30) Foreign Application Priority Data

Dec. 11, 2018 (CN) .......................... 201811510571.4

(51) Int. Cl.
C12P 7/62 (2022.01)
C12P 7/6427 (2022.01)
C12N 9/02 (2006.01)

(52) U.S. Cl.
CPC .......... *C12P 7/6427* (2013.01); *C12N 9/0071* (2013.01)

(58) Field of Classification Search
None
See application file for complete search history.

(56) References Cited

U.S. PATENT DOCUMENTS

| | | | | |
|---|---|---|---|---|
| 7,550,286 B2* | 6/2009 | Damude | ................... | A61P 3/00 435/254.2 |
| 7,615,364 B2* | 11/2009 | Shimizu | ................ | C12P 7/6409 435/189 |
| 8,962,276 B2* | 2/2015 | Chen | .................... | C12N 9/0071 435/69.1 |
| 9,115,339 B2* | 8/2015 | Chen | .................... | C12N 9/0071 |
| 9,315,836 B2* | 4/2016 | Chen | .................... | C12N 9/0071 |
| 2009/0325264 A1* | 12/2009 | Storek | ...................... | A23D 9/00 435/189 |
| 2014/0099683 A1* | 4/2014 | Chen | .................... | C12N 9/0071 435/134 |
| 2014/0363860 A1* | 12/2014 | Chen | .................... | C12P 7/6427 435/134 |
| 2021/0102225 A1* | 4/2021 | Song | .................... | C12N 9/0071 |

FOREIGN PATENT DOCUMENTS

| | | |
|---|---|---|
| CN | 102776213 A | 11/2012 |
| CN | 103820335 A | 5/2014 |
| CN | 110373437 A | 10/2019 |

OTHER PUBLICATIONS

Xiao Ruan, Improved Gama-linolenic acid production in Mucor circinelloides by homologous overexpressing of desaturases, Master's Thesis, Jiangnan University, Jun. 2015.
Shi et al., Molecular mechanism of substrate specifi city for delta 6 desaturase from Mortierella alpina and Micromonas pusilla, Journal of Lipid Research, vol. 56, pp. 2309-2321 (Oct. 20, 2015).
Ge et al., Application of a omega-3 Desaturase with an Arachidonic Acid Preference to Eicosapentaenoic Acid Production in Mortierella alpina, Front. Bioeng. Biotechnol. vol. 5, Article 89, pp. 1-10 (Jan. 22, 2018).
Rong et al., Molecular mechanism of substrate preference for omega-3 fatty acid desaturase from Mortierella alpina by mutational analysis and molecular docking, Applied Microbiology and Biotechnology, vol. 102, pp. 9679-9689 (Sep. 25, 2018).

* cited by examiner

*Primary Examiner* — Hope A Robinson
(74) *Attorney, Agent, or Firm* — SZDC Law P.C.

(57) ABSTRACT

Provided is construction of *Mucor circinelloides* cell factory for producing stearidonic acid (SDA) and fermentation technology. Δ15 Desaturase gene is obtained by cloning from *Mortierella alpina*, the gene is ligated to an integrative plasmid pMAT1552, and transformed into a *Mucor circinelloides* defective strain Mu402, and Δ15 Desaturase gene is integrated on *Mucor circinelloides* genome through homologous recombination, to obtain the recombinant strain Mc-Δ15, finally, the expression of the Δ15 Desaturase gene in *Mucor circinelloides* is realized. The recombinant new strain is accession number CGMCC No. 15888, and the classification name is *Mucor circinelloides*-D15D.

9 Claims, 1 Drawing Sheet
Specification includes a Sequence Listing.

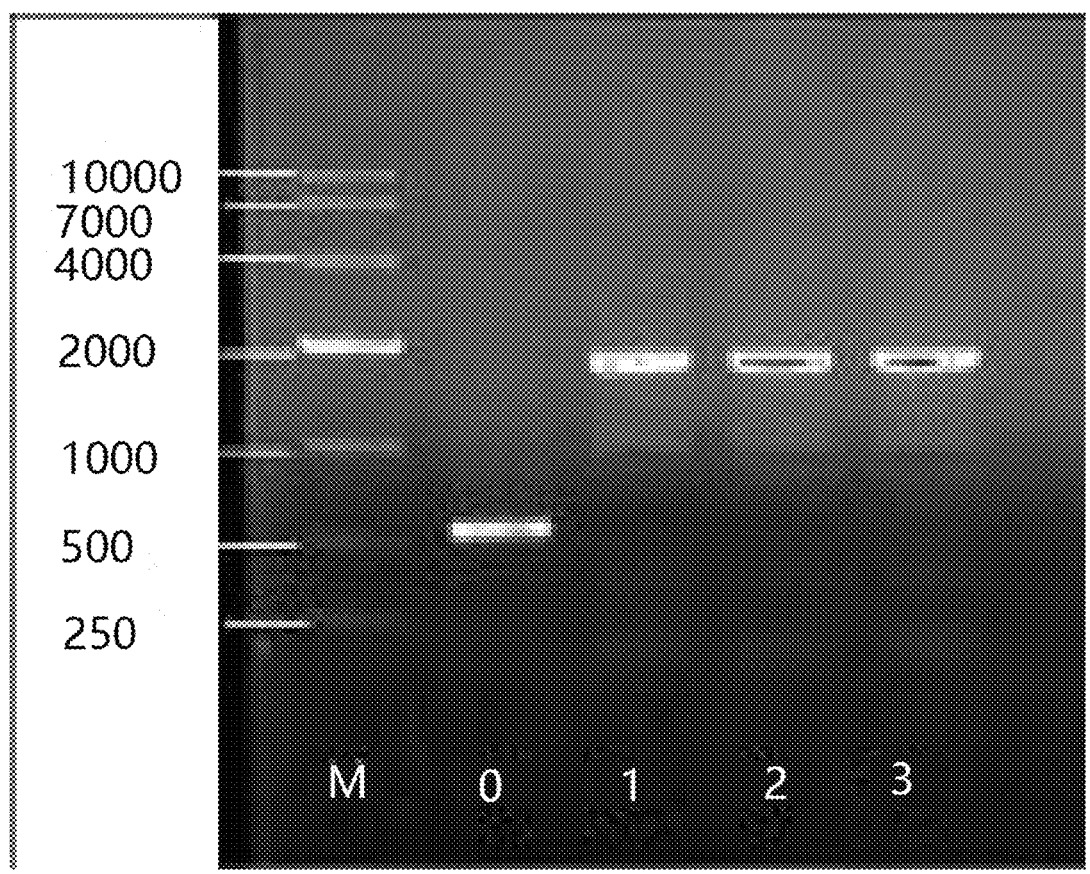

CONSTRUCTION OF *MUCOR CIRCINELLOIDES* CELL FACTORY FOR PRODUCING STEARIDONIC ACID AND FERMENTATION TECHNOLOGY THEREOF

CROSS-REFERENCE TO RELATED APPLICATION

The present application is a Continuation Application PCT/CN2019/124014, filed on Dec. 9, 2019, which claims the priority to the Chinese patent application with the filing number 201811510571.4, filed with the Chinese Patent Office on Dec. 11, 2018, and entitled "Construction of Mucor Circinelloides Cell Factory for Producing Stearidonic Acid and Fermentation Technology thereof", which is incorporated herein by reference in its entirety.

TECHNICAL FIELD

The present disclosure relates to construction of *Mucor circinelloides* cell factory for producing stearidonic acid and fermentation technology thereof, belonging to the field of genetic engineering. The present disclosure constructs a cell factory capable of producing stearidonic acid by heterologously expressing a Δ15 desaturase (Δ15 Des) in *Mucor circinelloides* using the technology of homologous recombination.

BACKGROUND ART

Microorganisms that accumulate more than 20% of lipids in cells are called as oleaginous microorganisms, including bacteria, fungi, yeasts and microalgae. Among lipid-producing fungi, *Mucor circinelloides* were used for industrial production of linolenic acid in the 1980s, and due to their high lipid-producing ability, genomes have been sequenced, and genetic research systems are well established, they are used as model organisms for researching the production of linolenic acid by microorganisms.

Polyunsaturated fatty acids (PUFAs) are gaining increasing attention due to their numerous nutritional and healthy benefits to the human body. Mammals, including humans, can only synthesize saturated fatty acids (SAFA) and mono-unsaturated fatty acids (MUFA) in vivo, while polyunsaturated fatty acids of the ω-6 and ω-3 series, such as linoleic acids (LA, 18:2, n-6) and α-linolenic acid (ALA, 18:3, n-3), cannot be synthesized in vivo. Hence, polyunsaturated fatty acids are essential fatty acids for the human body, and can only be obtained from diet. After being catalyzed by various enzymes, linoleic acid and linolenic acid can be used for synthesizing docosapentaenoic acid (DPA, 22:5, n-6) and docosahexaenoic acid (DHA, 22:5, n-3). Upon researches, it has been found that occurrence of various diseases, such as obesity, hypertension, diabetes, coronary sclerosis, schizophrenia and senile dementia, is associated with the metabolism of essential fatty acids. Therefore, essential fatty acids and their derivatives are of physiological and pathological importance for human health.

Stearidonic acid SDA (18:4n-3) is synthesized by α-linolenic acid ALA (18:3n-3) under the catalysis of Δ6 desaturase, or γ-linolenic acid (GLA, 18:3, n-6) under the catalysis of Δ15 Des. In the human body, the capacity of synthesizing SDA by ALA is quite limited, so that the actual significance of a strategy of adding human eicosapentaenoic acid EPA (20:5n-3) by supplementing ALA through diet is not great for human body, but the EPA, known as "blood vessel cleaner", has important physiological meanings for regulating blood lipid, reducing blood viscosity, and preventing thrombosis; lowering blood pressure, protecting the health of heart and cerebral vessels and the kidney function and so on, and SDA is easy to be converted into EPA in vivo. Therefore, it is of practical significance to directly increase SDA by diet, and further increase a synthesized amount of EPA in the human body. During the past 50 years, it has been generally accepted that increasing ω-3 fatty acids in the diet, especially EPA and DHA, can prevent a number of important factors causing occurrence of cardiovascular and cerebrovascular diseases, and EPA is a precursor of prostaglandin E3 and leukotriene B5.

*Mortierella alpina* is another lipid-producing microorganism, whose lipid yield can reach 50% of a dry weight of cells, and whose arachidonic acid (ARA) content is relatively high, therefore, *Mortierella alpina* is used for the industrial production of ARA. In recent years, many researches have been made on genes related to lipid production in *Mortierella alpina,* and the pathway of lipid synthesis thereof has been studied in detail. Δ15 Des is capable of catalyzing GLA (18:3, n-6) to produce SDA, thus, this gene is named as Δ15 Des, and this gene is a rate-limiting factor for arachidonic acid biosynthesis in *Mortierella alpina*. However, researches on the production of SDA using microbial expression of Δ15 Des are rare.

*Mortierella alpina* has relatively high oil yield and relatively high polyunsaturated fatty acid content, but its industrial application is limited due to its relatively high fermentation cost and low biomass. In earlier stage researches, our laboratory found that the GLA content in the fatty acid composition in the *Mucor circinelloides* cell is 18-19%, there is no SDA in the cell, but the fermentation conditions thereof are highly controllable and the biomass is high. Therefore, combining the advantages of two strains, the present research expresses the Δ15 Des derived from *Mortierella alpina* in *Mucor circinelloides* by the genetic engineering method of homologous recombination, to construct a cell factory capable of producing SDA, providing technical support for popularizing the industrial application of *Mucor circinelloides* to produce the SDA.

SUMMARY

The present disclosure provides construction of a *Mucor circinelloides* cell factory for producing stearidonic acid and fermentation technology thereof, including that Δ15 Des obtained by cloning from a *Mortierella alpina* strain is transferred into *Mucor circinelloides* by a homologous recombination method to obtain a *Mucor circinelloides* recombinant strain Mc-Δ15 for producing SDA, with a SDA content reaching 5.2%; and with a fatty acid precursor added, SDA functional lipid with a content of up to 8.3% is obtained by fermentation under an optimized fermentation process.

In one or more embodiments, the preparation method of the recombinant strain Mc-Δ15 in the present disclosure includes: with *Mortierella alpina* total cDNA being taken as a template, designing primers to perform PCR to obtain encoding Δ15 Des, whose nucleotide sequence is represented by SEQ ID NO: 1, ligating the gene to an integrative plasmid pMAT1552, then electrically transforming the recombinant plasmid into a protoplast of a *Mucor circinelloides* defective strain Mu402, and selecting a positive clone for fermentation culture.

In one or more embodiments, the optimized fermentation process of the recombinant strain Mc-Δ15 in the present disclosure includes: adding 1-3% safflower seed oil or sunflower seed oil into Kendrik culture medium, and culturing recombinant *Mucor circinelloides* cells under optimal fermentation parameters.

The recombinant cell for producing stearidonic acid provided in the present disclosure is characterized in that the recombinant cell includes a polynucleotide encoding Δ15 desaturase, and the polynucleotide encoding Δ15 desaturase is operably ligated to a promoter capable of directing the polynucleotide to be expressed in a cell.

In one or more embodiments, the recombinant cell is not derived from *Mortierella alpine*.

In one or more embodiments, the polynucleotide encoding Δ15 desaturase includes:

(1) a polynucleotide sequence represented by SEQ ID NO: 1;

(2) a polynucleotide sequence with at least 50%, preferably 60%, more preferably 70%, more preferably 80%, more preferably 90%, more preferably 95% identity to the polynucleotide sequence represented by SEQ ID NO: 1; or (3) a polynucleotide sequence encoding biologically active fragments among the polynucleotide sequence of (1) or (2).

In one or more embodiments, the recombinant cell is derived from a microbial cell, a plant cell or a microalgae cell.

In one or more embodiments, the recombinant cell is derived from a microbial cell, and the microbial cell of wild type substantially produces no stearidonic acid, In one or more embodiments, the microbial cell of wild type produces γ-linolenic acid, γ-linolenic acid compounds and/or precursor compounds of γ-linolenic acid.

In one or more embodiments, a content of the γ-linolenic acid in composition of fatty acid of the microbial cell of wild type is greater than 10%, for example, greater than 12%, for example, greater than 14%, for example, greater than 16%, and for example, greater than 18%.

In one or more embodiments, the recombinant cell is derived from a fungal cell.

In one or more embodiments, the recombinant cell is derived from a *Mucor* cell.

In one or more embodiments, the recombinant cell is derived from a *Mucor circinelloides* cell.

The present disclosure provides a method for preparing a recombinant cell for producing stearidonic acid in the present disclosure, wherein the method includes introducing into a cell a polynucleotide encoding Δ15 desaturase, wherein the polynucleotide encoding Δ15 desaturase is operably ligated to a promoter capable of directing the polynucleotide to be expressed in a cell.

The present disclosure provides a method for producing stearidonic acid, wherein the method includes fermenting the recombinant cell for producing stearidonic acid.

In one or more embodiments, the fermentation is carried out in fermentation culture medium, and the fermentation culture medium contains γ-linolenic acid, γ-linolenic acid compounds and/or precursor compounds of γ-linolenic acid.

In one or more embodiments, the fermentation culture medium contains linoleic acid and/or linoleic acid compounds.

In one or more embodiments, the fermentation culture medium contains vegetable oil containing linoleic acid and/or linoleic acid compounds.

In one or more embodiments, the vegetable oil is safflower seed oil and/or sunflower seed oil.

In one or more embodiments, the vegetable oil is initially present in the fermentation culture medium, or is added to the fermentation culture medium in a supplementing manner in a fermentation process.

The present disclosure provides a *Mucor circinelloides* recombinant strain Mc-Δ15, including integrated expression of Δ15 Des derived from *Mortierella alpina* on *Mucor circinelloides* genome. Compared with a contrast bacterium Mc1552, the fatty acid composition thereof is changed, and the SDA content reaches 5.2%, with precursor fatty acid being used as a substrate, the SDA content can reach 8.3% after the fermentation conditions are optimized.

The technical solution of the present disclosure is as follows: extracting mRNA of the *Mortierella alpina* strain to perform reverse transcription to obtain cDNA, designing specific primers to perform PCR to amplify Δ15 Des (the nucleotide sequence of which is represented by SEQ ID NO: 1), ligating the gene to an integrated plasmid pMAT1552, then electrically transforming the recombinant plasmid into a protoplast of a *Mucor circinelloides* defective strain Mu402, and selecting a positive clone to perform fermentation culture, wherein the fermentation conditions are as follows: using kendrick or improved Kendrick culture medium, 28° C., 700 rpm, an air inflow of 1 v/v min$^{-1}$, and pH 6.0. During the fermentation process, samples are collected according to the rule of lipid accumulation, to determine the lipid content and composition.

The present disclosure further provides a gene encoding Δ15 Des, and the nucleic acid sequence of the gene is represented by SEQ ID NO: 1.

The present disclosure further provides an expression vector containing SEQ ID NO:1, which can express Δ15 Des, and the vector is a *Mucor circinelloides* expression vector.

The recombinant new strain was preserved in China General Microbiological Culture Collection Center on Jun. 20, 2018, and the address is NO. 1 West Beichen Road, Chaoyang District, Beijing. The center gave the biological material the preservation number CGMCC No. 15888, and the suggested classification name is *Mucor circinelloides*-D15D.

Beneficial effects of the present disclosure, for example include: the present disclosure provides construction of *Mucor circinelloides* cell factory for producing SDA and fermentation technology thereof; the SDA content of the recombinant strain Mc-Δ15 can reach 8.3% of the total fatty acid.

BRIEF DESCRIPTION OF DRAWINGS

In order to more clearly illustrate technical solutions of embodiments of the present disclosure, the accompanying drawing which need to be used in the embodiments will be introduced below briefly.

FIG. 1 is a PCR verification chart of a *Mucor circinelloides* recombinant strain. In the drawing, M represents a standard protein molecular weight; 0 represents a control strain Mc1552; 1-3 represent a *Mucor circinelloides* recombinant strain Mc-Δ15.

DETAILED DESCRIPTION OF EMBODIMENTS

In order to make objects, technical solutions and advantages of the embodiments of the present disclosure clearer, the technical solutions in the embodiments of the present disclosure will be described clearly and completely below. If no specific conditions are specified in the embodiments, they are carried out under normal conditions or conditions recommended by the manufacturer. If the manufacturers of reagents or instrument used are not specified, they are conventional products commercially available.

Unless otherwise defined herein, scientific and technical terms used in connection with the present disclosure should have meanings that are commonly understood by those ordinarily skilled in the art. Exemplary methods and materials are described below, but methods and materials similar or equivalent to those described herein can also be used in the practice or test of the present disclosure.

As used herein, term "identity", "identity percentage" or "identity%" refers to a relationship of two or more nucleotide sequences (or polypeptide sequences) to one another as determined by sequence comparison. Identity may represent the degree of correlation of sequences between polynucleotides (or polypeptide sequences), and may be determined by the matching degree between character strings of such sequences. In one or more embodiments, the identity percentage of two sequences, whether nucleotide or amino acid sequences, is obtained by dividing the number of exact matches between the two compared sequences by the length of a shorter sequence, then multiplying the result by 100. For example, the polynucleotide encoding Δ15 desaturase includes a polynucleotide sequence having at least 50%, or at least 60%, or at least 70%, or at least 80%, or at least 85%, or at least 90%, or at least 95%, or at least 98%, or at least 99% identity to the polynucleotide sequence represented by SEQ ID NO: 1.

In one or more embodiments, the recombinant cell may be a cell of an organism suitable for fermentation, for example, a unicellular microorganism, which may be a prokaryote or a eukaryote such as yeast, or a plant cell. In one or more embodiments, the cell is a microbial cell. In one or more embodiments, the cell is a fungal cell.

In one or more embodiments, the recombinant cell of the present disclosure can be obtained upon transformation of a nucleic acid molecule into a cell accomplished by any method that involves inserting the nucleic acid molecule into the cell. Transformation techniques include, but are not limited to, transfection, electroporation, microinjection, lipofection, adsorption, and protoplast fusion. The recombinant cell may remain unicellular or may grow into tissue, organ or multicellular organism. The transformed nucleic acid molecule may remain extrachromosomal or the transformed nucleic acid molecule may be integrated into one or more sites within the chromosome of the transformed cell (i.e., recombinant cell) in a manner that retains its ability to be expressed.

In one or more embodiments, transformation of a nucleic acid molecule into a cell may be mediated by a recombinant vector. One type of recombinant vector includes a nucleic acid molecule of the present disclosure operably ligated to an expression vector. As indicated above, the words "operably ligate" refers to inserting a nucleic acid molecule into an expression vector in such a manner that the nucleic acid molecule can be expressed. The expression vector (which may be a DNA or RNA vector) is then capable of transforming a host cell and achieving expression of a specific nucleic acid molecule. In one or more embodiments, the expression vector is also capable of replication in a host cell. The expression vector may be a prokaryotic vector or a eukaryotic vector, and is typically virus or plasmid. The expression vector in the present disclosure includes any vector that is capable of functioning (i.e., directing gene expression) within a recombinant cell of the present disclosure.

As used herein, the term "biologically active fragment" herein refers to a portion of a given polypeptide/enzyme that still retains desaturase activity. These biologically active fragments can be readily determined by making a series of deletions to the full-length protein and testing activity of the resulting fragments.

When compared to a naturally occurring molecule, polynucleotides of the present disclosure may have one or more mutations that are deletions, insertions, or substitutions of nucleotide residues. The mutant may be naturally occurring (that is to say, isolated from a natural source) or synthesized (for example, synthesized by site-directed mutagenesis of a nucleic acid).

Example 1: Cloning of *Mortierella alpina* Δ15 Des

A *Mortierella alpina* strain was inoculated into a 500 mL Erlenmeyer flask equipped with a baffle and containing 100 mL of Kendrick culture medium (30 g/L glucose, 1.5 g/L $MgSO_4 \cdot 7H_2O$, 3.3 g/L ammonium tartrate, 7.0 g/L $KH_2PO_4$, 2.0 g/L $Na_2HPO_4$, 1.5 g/L yeast extract, 0.076 g/L $CaCl_2$, 8 mg/L $FeCl_3 \cdot 6H_2O$, 1 mg/L $ZnSO_4 \cdot 7H_2O$, 0.1 mg/L $CuSO_4 \cdot 5H_2O$, 0.1 mg/L $Co(NO_3)_2 \cdot 6H_2O$, 0.1 mg/L $MnSO_4 \cdot 5H_2O$), cultured at 28° C. and 150 rpm for 48 h, and thalli were collected by suction filtration. RNA was extracted, and reversely transcribed into cDNA, which was carried out with reference to instructions of a reverse transcription kit. According to the genome information of *Mortierella alpina* in NCBI database, Δ15 Des (KF 433065.1, 1212 bp) was found.

A nucleotide sequence (SEQ ID NO: 1) of Δ15 Des gene is as follows:

```
atggcacccc ctcacgttgt cgacgagcaa gtacgacgca gaatcgtcgt cgaggacgag atccagtcca agaagcagtt tgagcgcaac tatgtgccta tggactttac aatcaaggag attcgagatg cgatcccagc ccacctcttc atccgtgata ccacaaagtc gatcctgcat gtcgtcaagg atctggtcac tatcgccatc gttttttact gtgcaaccct catcgagact ctgccctcgc tcgctctgag agttcctgcc tggatcacct actggatcat ccaaggaact gtcatggtcg gcccctggat tctggcccac gagtgcggcc atggagcgtt ctcggacagc aagacgatca acaccatctt tggatgggtc cttcactctg ctcttttggt gccctaccag gcttgggcca tgtcgcattc caagcaccac aagggcactg gatccatgag caaggatgtc gttttcatcc ctgccactcg atcctacaag ggccttcccc cactggagaa gcctgccgcg gaagaggagg ttttggagca ggagcatcac caccatgaag agtccatctt tgctgagact cccatctaca ctctcggagc gcttttttc gtcctgacct tgggatggcc cttgtacttg atcatgaact tttctggaca cgaagcccct cactgggtca accacttcca gacggtcgcc cctctgtatg agcctcacca gcgcaagaac attttctact ccaactgcgg cattgtcgct atgggctcga tcctcactta
```

-continued

```
cctctcgatg gtcttctcgc ccttgactgt gttcatgtac tatggcatcc cctacctcgg agtcaatgct tggatcgtct gcatcaccta tctccagcac accgatccca aggtgcctca tttccgtgat aacgagtgga acttccagcg cggtgctgcc tgcactatcg accgatcctt cggtaccatt gtcaaccact tgcaccacca cattggtgac tctcatcaat gtcatcatat gttctcgcag atgcccttct acaacgccgt tgaggctaca aagcatctca aagccaagct tggcaagtac tacatatttg acgacactcc cattgccaag gccctctacc gcaattggag agagtgcaaa ttcgtggagg acgagggaga cgtagtgttc tacaagcatt ag
```

Specific primers Δ15-F and Δ15-R were designed according to the gene sequence, and PCR was carried out taking *Mortierella alpina* cDNA as a template.

Δ15-F:
(SEQ ID NO: 2)
5'-ACTTTTATATACAAAATAACTAAATCTCGAGATGGCACCCCCTCACG
TTG-3'

Δ15-R:
(SEQ ID NO: 3)
5'-ACTAGTCGCAATTGCCGCGGCTCGAGCTAATGCTTGTAGAACACTAC
G-3'

A 50 μL PCR reaction system: 10 μL of 5 ×PS buffer solution, 5 μL of dNTPs mixture (2 mM of each type), 1 μL of upstream primer, 1 μL of downstream primer, 100~200 ng of total cDNA, 1 μL of PrimeSTAR HS DNA polymerase, and ddH$_2$O for complementation to 50 μL. Reaction conditions were as follows: denaturation at 95° C. for 3 min, then starting cycling, then denaturation at 95° C. for 30 sec, annealing at 55° C. for 30 sec, extension at 72° C. for 1.5 min, after 30 cycles in total, extension again at 72° C. for 10 min, and reducing the temperature to 4° C. and keeping the temperature for 5 min. A 957 bp PCR fragment was obtained from amplification, the recovered fragment was ligated with a pMAT1552 vector, a ligated product transformed *Escherichia coli* Top10 competent cell, a transformed product was spread on an LB flat plate (10 g/L peptone, 5 g/L yeast cream, 10 g/L NaCl, and 1.5% agar) containing 100 mg/L ampicillin. The LB flat plate was cultured at 37° C. overnight, colonies were selected, and inoculated into an LB liquid culture medium (10 g/L peptone, 5 g/L yeast cream, and 10 g/L NaCl), after 8-10 h, plasmids were extracted for sequence determination, and the plasmids with correct sequences were named as pMAT1552-Δ15.

Preparation of *Mucor circinelloids* protoplasts: spores of *Mucor circinelloides* Mu402 strain were inoculated into a flat plate of YPG culture medium (3 g/L yeast extract, 10 g/L peptone, 20 g/L glucose, 20 μg/mL leucine, 200 μg/mL uracil, pH 4.5) and cultured at 28° C. for 1 day. The monoclonal hyphae were taken and dot-planted on a flat plate of YPG culture medium, and cultured at 28° C. for 3~4 days, then the spores could grow well. To each flat plate, on which the spores grew well, 5~6 mL of YPG culture medium was added, the spores were scraped with a sterilized spreading rod, a spore suspension was collected in a sterilized 50 mL centrifuge tube, and the concentration was calculated with a hemocytometer and the spore concentration was adjusted to 1×10$^7$/mL with YPG of pH 4.5. 12.5 mL of the above spore suspension was placed in a sterilized 250 mL Erlenmeyer flask, and placed in a refrigerator at 4° C. overnight to allow the spores to fully adsorb water and swell. The Erlenmeyer flask was placed on a shaker at 30° C. and 250 rpm to culture until the spores germinated. After centrifugation at 1100 rpm, the spores were washed twice with 5 mL of PS buffer of pH 6.5 [18.22 g of sorbitol and 20 mL of PBS buffer (137 mM NaCl, 2.7 mM KCl, 10 mM Na$_2$HPO$_4$, 2 mM KH$_2$PO$_4$)], to wash away the culture medium. The spores were resuspended in 5 mL of PS buffer, and lyase at a final concentration of 4 mg/mL and 0.06 U/mL chitosanase were added, followed by incubation on a shaker at 30° C. and 60 rpm for 90 min so as to remove cell walls. After centrifugation at 100×g, the spores were washed twice with 0.5 M sorbitol pre-cooled at 4° C., and 800 μL of 0.5 M sorbitol was added, followed by gentle pipetting for resuspension and precipitation to obtain protoplasts, which were dispensed for later use, with 100 μL in each tube.

Construction of recombinant strain Mc-Δ15: 100 μL of the protoplasts prepared above were uniformly mixed with 1 μg of plasmids pMAT1552-Δ15 or pMAT1552 to be subjected to electric shock transformation, after the electric shock was ended, 1 mL of pre-cooled YPGS (0.5 mol/L sorbitol, 3 g/L yeast extract, 10 g/L peptone, and 20 g/L glucose) was immediately added, for incubation at 26° C. and 100 rpm for 1 h, followed by centrifugation at 100×g to remove YPGS, after being resuspended in YNBS [91.1 g/L sorbitol, 1.5 g/L glutamic acid, 1.5 g/L (NH$_4$)$_2$SO$_4$, 0.5 g/L yeast basic nitrogen source, 10 g/L glucose, pH adjusted to 4.5, and after sterilization, thiamine and nicotinic acid were added to a final concentration of 1 μg/mL], the mixture was uniformly spread on an MMC selective culture medium [10 g/L casein amino acid, 0.5 g/L yeast basic nitrogen source, 20 g/L glucose, and 15 g/L agar, pH adjusted to 3.2, and after sterilization, thiamine and nicotinic acid were added to a final concentration of 1 μg/mL], followed by culturing in a light-tight condition at 28° C. for 3-4 days. Single colony hyphae growing on 8 selective flat plates were randomly selected to a new MMC flat plate, and cultured at 28° C. for 2-3 days to collect spores. About 200-300 spores were respectively inoculated to the MMC flat plate and the MMC flat plate containing uracil, and cultured at 28° C. for 2-3 days to count. The above screening steps were repeated until the number of the spores growing in the two flat plates was substantially the same, which indicated that the transformants with stable inheritance were obtained. The transformant hyphae with stable inheritance were cultured on a YPG culture medium flat plate at 30° C. for 5-7 days, then spores were collected, the concentration of the spores was adjusted to be 1×10$^7$/mL, and the spores were stored in a 30% glycerin tube at −80° C. Finally, the *Mucor circinelloides* recombinant strain Mc-Δ15 and the control strain Mc1552 were obtained. The residual thalli, cultured in the shake flask after the spreading, were isolated by vacuum filtration with a Buchner funnel, and the *Mucor circinelloides* genomic DNA was extracted (which was carried out by referring to the instructions of a plant rapid DNA extraction kit), which was taken as a template for PCR verification, with taking 1552-F and 1552-R as primers (this pair of primers were positions of 300bp upstream and downstream of a site of target gene inserted into the plasmid).

1552-F:

(SEQ ID NO: 4)
5'-CCTCGGCGTCATGATGTTTTTGTGTACCT-3'

1552-R:

(SEQ ID NO: 5)
5'-GGGATGTCTGCTGCTACCATGTCTCAT-3'

The reaction system and amplification conditions were as follows: pre-denaturation at 95° C. for 3 min, denaturation at 95° C. for 30 sec, annealing at 60° C. for 30 sec, extension at 72° C. for 2 min, with 30 cycles, and compensation extension at 72° C. for 10 min. The PCR verification results are shown as in FIG. 1. A fragment obtained for the *Mucor circinelloides* recombinant strain Mc-Δ15 has 1812 bp, while a fragment at the corresponding position of the control strain Mc1552 has 600 bp, which indicated that the plasmids had been successfully transformed into the *Mucor circinelloides*.

Fermentation Production of SDA Cell Factory:

(1) Fatty Acid Composition and Content Determination of *Mucor circinelloides* Recombinant Strain Mc-Δ15

Preparation of sample to be tested: the *Mucor circinelloides* recombinant strain Mc-Δ15 was cultured in a 2 L fermentation tank using Kendrick culture medium. The fermentation conditions were as follows: 28° C., 700 rpm, an air inflow of 1 v/v min$^{-1}$, and pH being maintained at 6.0. According to the oil production rule of *Mucor circinelloides*, a whole fermentation broth sample was collected and subjected to vacuum filtration with a Buchner funnel, then the fermentation broth and thalli were separated, the fermentation broth was collected and stored at −20° C. for later use, and the thalli were washed with distilled water for 3 times, and then freeze-dried for later use.

Using the cell disruption method of acid treatment combined with multigelation, lipids were extracted from thalli of the recombinant bacteria Mc-Δ15 with an organic solvent, referring to the method (Folch J, Lees M, Sloane-Stanley G, et al. A simple method for the isolation and purification of total lipids from animal tissues. Biol Chem, 1957, 226, 497-509) with appropriate modifications. The specific method was as follows: (1) after grinding the freeze-dried thalli, weighing 20 mg dry weight of thalli in a 5 mL glass bottle, and adding 2 mL of 4 M hydrochloric acid thereto; (2) subjecting the glass bottle to a 80° C. water bath for 1 h, and at −80° C. for 15 min, and repeating the process once; (3) after the glass bottle returns to room temperature, adding 1 mL of methanol and 1 mL of chloroform, and adding 100 μL of internal standard C15:0 with a concentration of 2.02 μg/μL by a microsyringe; (4) subjecting the glass bottle to rotational extraction for 0.5 h with a mixer, followed by centrifugation at 3000 rpm for 3 min, and collecting a chloroform layer in a new 5 mL glass bottle; (5) adding 1 mL of chloroform to the original glass bottle again, repeating the process of (4) and combining the chloroform layers; (6) blowing dry with nitrogen; (7) adding 1 mL of 10% methanolic hydrochloric acid solution, subjecting the original glass bottle to a 60° C. water bath for 3 h, during which the bottle was shaken for 30 sec every half hour; (8) after the bottle was cooled to room temperature, adding 2 mL of n-hexane and 1 mL of saturated NaCl solution, mixing well by vortex oscillation, centrifuging at 4000 rpm for 3 min, then taking 1 mL of n-hexane layer, and transferring to a gas-phase bottle to obtain a fatty acid methyl ester solution.

Fatty acid methyl ester was analyzed by gas chromatography with taking commercial fatty acid methyl ester standards (37 fatty acid methyl ester mixed standards) as standard samples. The gas chromatography was performed by GC-6890N of Agilent, USA, and the measurement conditions were as follows: gas chromatography conditions: split-less sampling, using DM-FFAP (30 m×0.32 mm, 0.22 μm) as chromatographic column, a hydrogen ion flame detector, and nitrogen as the carrier gas, the temperature of a gasification chamber and the temperature of the detector both being 250° C., and a sample size of 1 μL. A temperature rising process: an initial temperature was 80° C., the temperature was first increased to 200° C. at a heating rate of 8° C./min, then increased to 205° C. at a heating rate of 1° C./min, and finally increased to 240° C. at a heating rate of 4° C./min, and the temperature was kept for 5 min. Taking pentadecanoic acid (C15:0) as a reference, the size of the peak area of each fatty acid composition was recorded, and the content of total fatty acid was calculated. The results are as shown in Table 1, in which the intracellular lipid content of the over-expressed strain Mc-Δ15 is increased.

TABLE 1

Lipid Contents of Control Strain and Δ15 Over-expressed Strain by Fermentation Culture

| | Fermentation Time (h) | 12 | 24 | 36 | 48 | 60 | 72 | 84 | 96 |
|---|---|---|---|---|---|---|---|---|---|
| Strains | Mc-Δ15 | 3.75 | 6.78 | 12.11 | 14.92 | 15.53 | 15.34 | 15.32 | 15.29 |
| | Mc1552 | 5.8 | 9.2 | 11.7 | 12.3 | 12.4 | 12.6 | 13.2 | 13.1 |

The fatty acid composition of intracellular lipid of the over-expressed strain Mc-Δ15 changed greatly, and SDA was contained in the lipid of the over-expressed strain Mc-Δ15, of which the content reached 5.2% of the total fatty acid content. The results are as shown in Table 2.

TABLE 2

Fatty Acid Composition of Lipids of Control Strain and Δ15 Des Over-expressed Strain by Fermentation Culture

| Fatty Acid composition (%) | | C (16:0) | C (18:0) | C (18:1) OA | C (18:2) LA | C (18:3) GLA | C (18:4) SDA |
|---|---|---|---|---|---|---|---|
| Strains | Mc-Δ15 | 16.4 | 3.7 | 30.2 | 16.2 | 21.2 | 5.2 |
|  | Mc1552 | 18.4 | 4.2 | 31.5 | 16.8 | 29.8 | 0 |

(2) Fatty Acid Composition and Content Determination of *Mucor circinelloides* Recombinant Strain Mc-Δ15 Under Optimized Fermentation Conditions Preparation of sample to be tested: the *Mucor circinelloides* recombinant strain Mc-Δ15 was cultured in a 2 L fermentation tank using improved Kendrick culture medium (adding safflower oil rich in linoleic acid to the culture medium). The fermentation conditions were as follows: 28° C., 700 rpm, an air inflow of 1 v/v min$^{-1}$, and pH being maintained at 6.0. According to the oil production rule of *Mucor circinelloides*, a whole fermentation broth sample was collected and subjected to vacuum filtration with a Buchner funnel, to separate the fermentation broth and thalli, the fermentation broth was collected and stored at −20° C. for later use, and the thalli were washed with distilled water for 3 times, and then freeze-dried for later use.

Using the cell disruption method of acid treatment combined with multigelation, lipids were extracted from thalli of the recombinant bacteria Mc-Δ15 with an organic solvent, referring to the method (Folch J, Lees M, Sloane-Stanley G, et al. A simple method for the isolation and purification of total lipids from animal tissues. Biol Chem, 1957, 226, 497-509) with appropriate modifications. The specific method was as follows: (1) after grinding the freeze-dried thalli, weighing 20 mg dry weight of thalli in a 5 mL glass bottle, and adding 2 mL of 4 M hydrochloric acid thereto; (2) subjecting the glass bottle to a 80° C. water bath for 1 h, and at −80° C. for 15 min, and repeating the process once; (3) after the glass bottle returns to room temperature, adding 1 mL of methanol and 1 mL of chloroform, and adding 100 μL of internal standard C15:0 with a concentration of 2.02 μg/μL by a microsyringe; (4) subjecting the glass bottle to rotational extraction with a mixer for 0.5 h, followed by centrifugation at 3000 rpm for 3 min, and collecting a chloroform layer in a new 5 mL glass bottle; (5) adding 1 mL of chloroform to the original glass bottle again, repeating the process of (4) and combining the chloroform layers; (6) blowing dry with nitrogen; (7) adding 1 mL of 10% methanolic hydrochloric acid solution, subjecting the original glass bottle to a 60° C. water bath for 3 h, during which the bottle was shaken for 30 sec every half hour; (8) after the bottle was cooled to room temperature, adding 2 mL of n-hexane and 1 mL of saturated NaCl solution, mixing well by vortex oscillation, centrifuging at 4000 rpm for 3 min, taking 1 mL of n-hexane layer, and transferring to a gas-phase bottle to obtain a fatty acid methyl ester solution.

Fatty acid methyl ester was analyzed by gas chromatography with taking commercial fatty acid methyl ester standards (37 fatty acid methyl ester mixed standards) as standard samples. The gas chromatography was performed by GC-6890N of Agilent, USA, and the measurement conditions were as follows: gas chromatography conditions: splitless sampling, using DM-FFAP (30 m×0.32 mm, 0.22 μm) as chromatographic column, a hydrogen ion flame detector, and nitrogen as the carrier gas, the temperature of a gasification chamber and the temperature of the detector both being 250° C., and a sample size of 1 μL. A temperature rising process: an initial temperature was 80° C., the temperature was first increased to 200° C. at a heating rate of 8° C./min, then increased to 205° C. at a heating rate of 1° C./min, and finally increased to 240° C. at a heating rate of 4° C./min, and the temperature was kept for 5 min. Taking pentadecanoic acid (C15:0) as a reference, the size of the peak area of each fatty acid composition was recorded, and the content of total fatty acid was calculated. The results are as shown in Table 3, in which the intracellular lipid content of the over-expressed strain Mc-Δ15 is increased.

TABLE 3

Lipid Contents of Control Strain and Δ15 Over-expressed Strain by Fermentation Culture

| | Fermentation Time (h) | 12 | 24 | 36 | 48 | 60 | 72 | 84 | 96 |
|---|---|---|---|---|---|---|---|---|---|
| Strains | Mc-Δ15 | 4.2 | 6.5 | 11.9 | 14.8 | 15.7 | 15.6 | 15.4 | 15.3 |
|  | Mc1552 | 5.8 | 9.4 | 11.5 | 12.2 | 12.7 | 12.6 | 13.3 | 13.2 |

The fatty acid composition of intracellular lipid of the over-expressed strain Mc-Δ15 changed greatly, and SDA appeared in the lipid of the over-expressed strain Mc-Δ15, of which the content reached 8.3% of the total fatty acid content. The results are as shown in Table 4.

TABLE 4

Fatty Acid Composition of Lipids of Control Strain and Δ15 Over-expressed Strain by Fermentation Culture

| Fatty Acid composition (%) | | C (16:0) | C (18:0) | C (18:1) OA | C (18:2) LA | C (18:3) GLA | C (18:4) SDA |
|---|---|---|---|---|---|---|---|
| Strains | Mc-Δ15 | 16.7 | 3.6 | 3.07 | 15.7 | 21.3 | 8.3 |
| | Mc1552 | 18.5 | 4.3 | 31.3 | 16.7 | 29.6 | 0 |

The above-mentioned are merely for preferred embodiments of the present disclosure, and not intended to limit the present disclosure. For one skilled in the art, various modifications and variations may be made to the present disclosure. Any amendments, equivalent replacements, improvements and so on, made within the spirit and principle of the present disclosure, should be covered within the scope of protection of the present disclosure.

INDUSTRIAL APPLICABILITY

The present disclosure provides construction of *Mucor circinelloides* cell factory for producing SDA and fermentation technology thereof; the SDA content of the recombinant strain Mc-Δ15 can reach 8.3% of the total fatty acid. Therefore, the recombinant strain Mc-Δ15 can be used to produce stearidonic acid.

What is claimed is:

1. A recombinant cell for producing stearidonic acid, wherein the recombinant cell comprises a polynucleotide encoding Δ15 desaturase, and the polynucleotide encoding Δ15 desaturase is operably ligated to a promoter that directs the polynucleotide to be expressed in a cell,
   wherein the polynucleotide encoding Δ15 desaturase comprises the polynucleotide sequence set forth in SEQ ID NO: 1, and
   wherein the recombinant cell is obtained from a *Mucor* cell.

2. The recombinant cell of claim 1, wherein the recombinant cell is obtained from a *Mucor circinelloides* cell.

3. A method for preparing a recombinant cell for producing stearidonic acid, the method comprising:
   introducing into the cell a polynucleotide encoding Δ15 desaturase,
   wherein the polynucleotide encoding the Δ15 desaturase is operably ligated to a promoter that directs the polynucleotide to be expressed in the cell,
   wherein the polynucleotide encoding Δ15 desaturase comprises
   the polynucleotide sequence set forth in SEQ ID NO: 1, and
   wherein the recombinant cell is obtained from a *Mucor* cell.

4. A method for producing stearidonic acid in a recombinant cell, comprising:
   introducing into the recombinant cell a polynucleotide encoding Δ15 desaturase,
   wherein the polynucleotide encoding Δ15 desaturase is operably ligated to a promoter that directs the polynucleotide to be expressed in the cell; and
   fermenting the recombinant cell to produce stearidonic acid,
   wherein the polynucleotide encoding Δ15 desaturase comprises the polynucleotide sequence set forth in SEQ ID NO: 1; and
   wherein the recombinant cell is obtained from a *Mucor* cell.

5. The method of claim 4, wherein the fermenting is carried out in a fermentation culture medium, and the fermentation culture medium comprises linolenic acid, linolenic acid compounds and/or precursor compounds of linolenic acid.

6. The method of claim 5, wherein the fermentation culture medium comprises γ-linolenic acid and/or γ-linolenic acid compounds.

7. The method of claim 5, wherein the linolenic acid and/or the linolenic acid compounds are in a vegetable oil.

8. The method of claim 7, wherein the vegetable oil is a safflower seed oil and/or a sunflower seed oil.

9. The method of claim 7, wherein the vegetable oil is initially present in the fermentation culture medium, or is added to the fermentation culture medium as a supplement during fermenting.

* * * * *

SEQUENCE LISTING

<160> NUMBER OF SEQ ID NOS: 5

<210> SEQ ID NO 1
<211> LENGTH: 1212
<212> TYPE: DNA
<213> ORGANISM: Mortierella alpina

<400> SEQUENCE: 1

```
atggcacccc ctcacgttgt cgacgagcaa gtacgacgca gaatcgtcgt cgaggacgag      60
atccagtcca agaagcagtt tgagcgcaac tatgtgccta tggactttac aatcaaggag     120
attcgagatg cgatcccagc ccacctcttc atccgtgata ccacaaagtc gatcctgcat     180
gtcgtcaagg atctggtcac tatcgccatc gtttttttact gtgcaacctt catcgagact     240
ctgccctcgc tcgctctgag agttcctgcc tggatcacct actggatcat ccaaggaact     300
gtcatggtcg gcccctggat tctggcccac gagtgcggcc atggagcgtt ctcggacagc     360
aagacgatca acaccatctt tggatgggtc cttcactctg ctcttttggt gccctaccag     420
gcttgggcca tgtcgcattc caagcaccac aagggcactg gatccatgag caaggatgtc     480
gttttcatcc ctgccactcg atcctacaag ggccttcccc cactggagaa gcctgccgcg     540
gaagaggagg ttttggagca ggagcatcac caccatgaag agtccatctt tgctgagact     600
cccatctaca ctctcggagc gcttttttc gtcctgacct tgggatggcc cttgtacttg     660
atcatgaact tttctggaca cgaagcccct cactgggtca accacttcca gacggtcgcc     720
cctctgtatg agcctcacca gcgcaagaac attttctact ccaactgcgg cattgtcgct     780
atgggctcga tcctcactta cctctcgatg gtcttctcgc ccttgactgt gttcatgtac     840
tatggcatcc cctacctcgg agtcaatgct tggatcgtct gcatcaccta tctccagcac     900
accgatccca aggtgcctca tttccgtgat aacgagtgga acttccagcg cggtgctgcc     960
tgcactatcg accgatcctt cggtaccatt gtcaaccact tgcaccacca cattggtgac    1020
tctcatcaat gtcatcatat gttctcgcag atgcccttct acaacgccgt tgaggctaca    1080
aagcatctca aagccaagct tggcaagtac tacatatttg acgacactcc cattgccaag    1140
gccctctacc gcaattggag agagtgcaaa ttcgtggagg acgagggaga cgtagtgttc    1200
tacaagcatt ag                                                        1212
```

<210> SEQ ID NO 2
<211> LENGTH: 50

```
<212> TYPE: DNA
<213> ORGANISM: Artificial Sequence
<220> FEATURE:
<223> OTHER INFORMATION: Primer

<400> SEQUENCE: 2
acttttatat acaaataac taaatctcga gatggcaccc cctcacgttg            50

<210> SEQ ID NO 3
<211> LENGTH: 48
<212> TYPE: DNA
<213> ORGANISM: Artificial Sequence
<220> FEATURE:
<223> OTHER INFORMATION: Primer

<400> SEQUENCE: 3
actagtcgca attgccgcgg ctcgagctaa tgcttgtaga acactacg             48

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
cctcggcgtc atgatgtttt tgtgtacct                                  29

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
gggatgtctg ctgctaccat gtctcat                                    27
```